United States Patent [19]

Carim

[11] Patent Number: 4,846,185
[45] Date of Patent: Jul. 11, 1989

[54] BIOELECTRODE HAVING A GALVANICALLY ACTIVE INTERFACING MATERIAL

[75] Inventor: Hatim M. Carim, St. Paul, Minn.

[73] Assignee: Minnesota Mining and Manufacturing Company, St. Paul, Minn.

[21] Appl. No.: 125,138

[22] Filed: Nov. 25, 1987

[51] Int. Cl.⁴ .............................................. A61B 5/04
[52] U.S. Cl. ................................................... 128/641
[58] Field of Search ............................. 128/639–641, 128/798, 802, 803

[56] References Cited

U.S. PATENT DOCUMENTS

| | | |
|---|---|---|
| 3,096,202 | 7/1963 | Degroot von Arx . |
| 3,252,995 | 5/1966 | Grosser et al. . |
| 3,294,765 | 12/1966 | Hort et al. ............................ 260/80.3 |
| 3,532,679 | 10/1970 | Steckler . |
| 3,566,860 | 3/1971 | Moe, Jr. ............................ 128/2.1 E |
| 3,689,439 | 9/1972 | Field et al. . |
| 3,759,880 | 9/1973 | Hoffman et al. . |
| 3,805,769 | 4/1974 | Sessions ........................... 128/2.06 E |
| 3,907,720 | 9/1975 | Field et al. . |
| 3,911,906 | 10/1975 | Reinhold, Jr. ....................... 128/641 |
| 3,925,282 | 12/1975 | Davis et al. . |
| 3,976,055 | 8/1976 | Monter et al. .................. 128/2.06 E |
| 4,066,078 | 1/1978 | Berg ................................... 128/2.06 |
| 4,094,822 | 6/1978 | Kater ................................ 252/2.06 E |
| 4,102,331 | 7/1978 | Grayzel et al. ...................... 128/512 |
| 4,109,648 | 8/1978 | Larke et al. ..................... 128/2.06 E |
| 4,273,135 | 6/1981 | Larimore et al. .................... 128/640 |
| 4,352,359 | 10/1982 | Larimore et al. .................... 128/640 |
| 4,364,972 | 12/1982 | Moon . |
| 4,377,170 | 3/1983 | Carim ................................ 128/639 |
| 4,391,278 | 7/1983 | Cahalan et al. ..................... 128/640 |
| 4,406,827 | 9/1983 | Carim ................................ 252/518 |
| 4,524,087 | 6/1985 | Engel .................................. 427/2 |
| 4,536,554 | 8/1985 | Lim et al. ........................... 526/264 |
| 4,539,996 | 9/1985 | Engel ................................ 128/640 |
| 4,554,924 | 11/1985 | Engel ................................ 128/640 |
| 4,727,880 | 3/1988 | Roberts ............................. 128/640 |

FOREIGN PATENT DOCUMENTS

| | | | |
|---|---|---|---|
| 0085327 | 8/1983 | European Pat. Off. ............ 128/640 |
| 0107376 | 9/1983 | European Pat. Off. . |
| 2159639 | 7/1987 | Japan ................................. 128/641 |
| 1511563 | 6/1975 | United Kingdom . |
| 2115431 | 2/1983 | United Kingdom . |
| 8605083 | 9/1986 | World Int. Prop. O. ........... 128/641 |

OTHER PUBLICATIONS

A. G. Sykes, "Metal-Ion Complexes and Their Redox Properties", *Chemistry in Brittain*, vol. 6, No. 4, pp. 159–164 (1970).
"Ion-Selective Electrode", author unknown, *Research Disclosure*, No. 16113, pp. 29–39, Sept. 1977.

Primary Examiner—Lee S. Cohen
Attorney, Agent, or Firm—Donald M. Sell; Walter N. Kirn; Dale E. Hulse

[57] ABSTRACT

A biomedical electrode comprised of a galvanically inert sensing element and a galvanically active interfacing material containing oxidizable and reducible species such as ferrous/ferric sulfate is disclosed. The bioelectrode recovers from overload potentials (e.g., defibrillation potentials) as well as conventional silver/silver chloride electrodes and can be made at a much lower cost from non-corrosive materials.

18 Claims, 1 Drawing Sheet

BIOELECTRODE HAVING A GALVANICALLY ACTIVE INTERFACING MATERIAL

FIELD OF THE INVENTION

This invention relates to the field of disposable biomedical electrodes, particularly those used to pick up electrical signals from the body to obtain an electrocardiogram. Another aspect of the invention relates to a galvanically active interfacing material used in such electrodes to enhance electrical connection between a galvanically inert sensing element and a patient's skin.

BACKGROUND ART

A large number of disposable biomedical electrodes for heartbeat monitoring and the like are currently available. Such electrodes are designed to detect variations in the electrical potentials which appear on the skin of a patient and which reflect heartbeat or other electrophysiological activity. Since these skin potentials are very small, e.g., on the order of 2 millivolts, the potentials must be amplified considerably to provide effective outputs reflecting the electrophysiological activity of interest. For this reason, electrodes must have very high performance to minimize noise factors and maximize the quality of the signals transmitted to the testing apparatus. An electrolyte, typically a gel or adhesive film, is generally used to enhance electrical connection between a sensing element of the electrode and the skin.

Electrodes used to obtain electrocardiograms (ECG) should also be able to recover from polarizing overloads. Polarization occurs when an extraneous external voltage is applied to the patient wearing the electrode (e.g. defibrillation voltage) and the electrode is not able to function. An ECG electrode which can recover from the superimposition of a large defibrillation current in a relatively short period of time is important to detecting whether the defibrillation procedure has started the heart. Thereafter the electrode needs to continue to pick up the tiny voltages associated with the heart's beating without loss of fidelity of the signal. The electrode needs to recover to a half-cell potential approaching its original half-cell potential. When the instrument used with the electrode has a very high quality input amplifier, the half-cell potential does not need to recover to the same extent required with lower quality instruments The electrode at a minimum should recover so that its polarization (the difference between its new half-cell potential and its original half-cell potential) is no greater than 300 millivolts. Preferably polarization should be no greater than 100 millivolts after 5 seconds after four defibrillation pulses.

Electrodes exist which are sufficiently non-polarizable. These perform well by virtue of their being highly reversible That is, the chemical reactions which occur when an electric current passes through the electrode are completely and immediately reversible. The electric current itself is composed of the movement of charged ions through the electrolyte which forms the interface between the skin and the sensing element of the electrode. When these ionic currents meet the sensing element, normally a "metallic" conductor, they are converted into electronic currents which are carried by wires, switched, detected, amplified, and so on in instruments such as an electrocardiograph machine. These reactions at the sensing elements are often upset by the superimposition of external voltages, resulting in a polarized electrode.

In the bioelectrode art, a sensing element made from silver/silver chloride has become the standard for high quality electrodes of low polarizability. U.S. Pat. No. 4,377,170 (to Carim) describes one silver/silver chloride nonpolarizable electrode. In electrodes of this type an element body made of (or coated with) silver is coated, either mechanically or by chemical reaction, with silver chloride The electrolyte, e.g., sodium chloride or the like as the ionic-conducting species, is frequently contained within an aqueous gel or as an aqueous solution held in a sponge. This type of electrode, though it can work quite satisfactorily, has two major disadvantages. It has a high cost, because of the need to use silver, and corrosion is a problem, because of the presence of corrosive sodium chloride solution High cost is partially alleviated by substituting cheaper materials for at least a portion of the silver in the sensing element Such elements made by silver-plating molded plastic are well known. However, the process of accurately and reproducibly depositing a silver coating onto a plastic substrate requires careful control, as does the subsequent conversion of the silver surface to a silver chloride surface. In addition, malfunction of the electrode can occur through chemical reaction between the sensing element and the electrolyte and also through corrosion of other parts of the electrode, such as the metallic snap connector frequently used to connect the lead wire to the sensor.

Sensing elements made of materials other than silver/silver chloride have been used in biomedical electrodes. The use of nonmetallic, noncorrosive sensing elements made of carbon or carbon-containing molded plastics is disclosed in U.S. Pat. Nos. 3,566,860 and 4,109,648. However, these elements are highly polarizable when used with known electrolytes and they are generally unsuitable for use in monitoring electrodes. U.S. Pat. No. 3,976,055 (to Monter et al.) describes an electrode in which an electrically conductive but galvanically inactive sensing element such as carbon-impregnated plastic has one or more metal particles anchored to the surface of the sensing element at the interface between the electrolyte and the galvanically inactive sensing element.

SUMMARY OF THE INVENTION

According to the present invention, a galvanically inactive sensing element, such as a carbon or graphite sensing element, can be utilized in a bioelectrode by the use of a novel interfacing material between the sensing element and the skin. As a result, high performance comparable to a silver/silver chloride electrode can be achieved at lower cost without corrosion problems.

According to the present invention, a bioelectrode comprises (1) an electrically-conductive, electrochemically-inert sensing element; (2) a conformable, dermatologically-compatible electrically-conductive interfacing material in electrical contact with the sensing element; and (3) means for maintaining the interfacing material in contact with the skin The interfacing material contains an oxidizable species and a reducible species in solution in amounts sufficient to be galvanically active at the interface of the sensing element and the interfacing material so that the electrode recovers from overload potentials sufficiently to transmit a biological signal. Preferably the interfacing material contains an oxidizable and reducible species in amounts sufficient for the electrode to recover to a polarization not greater than 300 millivolts. Most preferably the interfacing material contains oxidizable and reducible species in amounts sufficient for the electrode to recover to a polarization not greater than 100 millivolts after 5 seconds of a fourth overload pulse.

In the preferred bioelectrodes of this invention, the sensing element is formed of graphite and the interfacing material is a gel or adhesive containing a ferrous/ferric redox couple To stabilize the interfacing material at the pH most compatible with skin, inclusion of a chelating agent such as ethylenediaminetetraacetic acid (EDTA) is also preferred.

DETAILED DESCRIPTION OF THE INVENTION

Figure 1:
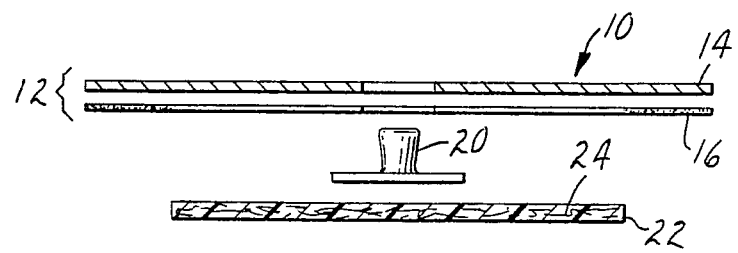
FIG. 1 is an exploded sectional view of a disposable ECG electrode having the inert sensing element and interfacing material of the present invention.

The sensing element of the bioelectrode is an electrically-conductive, electrochemically-inert member which, in the case of a sensing electrode such as an ECG electrode, picks up electrical impulses from the skin and transmits them to an apparatus such as an electrocardiograph, or, in the case of a stimulating electrode such as a TENS electrode, distributes electrical current from a stimulator to the skin beneath the electrode. The term "electrochemically-inert", as used herein, means any material that is galvanically inactive and which will not substantially corrode while in contact with the interfacing material over the useful life of the bioelectrode. Examples of suitable electrochemically-inert materials include the noble metals, such as platinum, gold, palladium, iridium and their alloys, and the electrically-conductive forms of carbon, e.g., graphite, alone or as a filler in a polymeric binder such as polyester, polyethylene-vinyl acetate (EVA), etc Graphite is preferred because of its relatively low cost. When the interfacing material does not have particularly corrosive ions, non-noble metals which have been made corrosion resistant, e.g., stainless steel, may be used.

The sensing element is preferably in the shape of an eyelet comprised of a planar base having generally coplanar upper and lower surfaces and a post integral with the upper surface of the base and extending from it. The preferred eyelet is comprised of powdered graphite dispersed in a binder, e.g. those available from Fiberite Corp., Winona, MN. Other suitable graphite eyelets of the sintered graphite type are available from Schunk and Ebe of West Germany.

The interfacing material may be comprised of water and a hydrocolloid gelling material. Examples of suitable hydrocolloids include polysaccharides such as gel-forming starches and natural gums, e g., guar gum and locust bean gum, polysaccharide derivatives such as cellulose ethers, and hydrophilic synthetic polymers such as polyacrylic acids and polyacrylamides having molecular weights sufficient to gel a solution of a biologically acceptable redox couple. The concentration of the hydrocolloid in the gel generally ranges from about 0.5% by weight to 60% by weight with the preferred ranges for several hydrocolloids shown in Tables 1-4 below. Other interfacing materials include a gel pad soaked with an electrolyte solution as disclosed in U.S. Pat. No. 3,805,769 (Sessions).

The interfacing material contains biologically acceptable, i.e., dermatologically non-irritating and non-toxic, oxidizable and reducible species. The interfacing material includes sufficient amounts of the oxidizable and reducible species for the electrode to recover from overload potentials The oxidizable and reducible species are present in the gel as ionic species. Ferric/ferrous couples such as ferric sulfate/ferrous sulfate are preferred Redox couples such as the quinhydrone couple, stannous/stannic, and cobaltous/cobaltic provide good non-polarizability, however, these couples are less preferred from the standpoint of dermatological compatibility.

In general, the combined concentration of the oxidizable and reducible species may vary somewhat but an equimolar mixture is preferred, e.g., a 1:1 molar mixture of ferric and ferrous ions is preferred.

The level of oxidizable and reducible species needed depends upon the particular gel/adhesive composition. In a simple solution such as the following:

|  | wt. % |
|---|---|
| Ferrous sulfate | .2 |
| Ferric sulfate | .2 |
| Water | 69.6 |
| Glycerol | 30 | the low levels of the iron salts are quite adequate to give a relatively non-polarizable electrode with a carbon-containing conductor. However, if a thickening agent or other ingredient is present which complexes the iron salts or if other ingredients cover the surface of the sensing element, the amount of iron species in solution at the interface of the sensing element and the interfacing material is reduced and thus the reaction of the iron species with the surface of the sensing element is hindered. In such a case, the concentration of the iron salts in solution must be increased by increasing the amount of iron salts added to the interfacing material. Also, the higher the pH of the interfacing material, the greater is the tendency for the iron salts to form oxides and hydroxides, thereby lowering their useful, effective concentration in solution and at the gel/sensing element interface. The optimum concentrations of the oxidizable and reducible species in a particular interfacing material are readily determinable empirically using the test methods described below.

In order to be useful in a bioelectrode, the oxidizable and reducible species of the interfacing material should be dermatologically compatible. In particular, for long term use of the electrode, i.e. application to skin for over about 3 hours, the oxidizable and reducible species are preferably operative in an interfacing layer having a pH between about 3.5 and about 8. (If desired, an appropriate pH buffer, for example, disodium citrate, may be added to the interfacing material to more carefully maintain the pH within this range.) For short term use, e.g., 1 to 3 hours, a pH range of from 1.5 to 9 is acceptable. In this regard, while the preferred oxidizable and reducible species, i.e., the ferrous/ferric redox couple, is non-toxic, the ferrous and ferric cations are optimally soluble in water only at a pH of about 1.6 to 2.2, unless a complexing (or sequestering) agent is used. Suitable complexing agents that can be used to complex the ferrous and ferric ions at a dermatologically acceptable pH include ethylenediaminetetraacetic acid (EDTA) and nitrilotriacetic acid (NTA).

The oxidizable and reducible species may be incorporated into a number of different types of electrically-conductive solutions, gels and/or adhesives to form the interfacing material. Some presently preferred embodiments include the electrically-conductive adhesives described and claimed in U.S. application Ser. No. 125,406, filed on even date herewith by D. Duan, the disclosure of which is incorporated herein by reference.

The electrically-conductive adhesives described in the foregoing concurrently filed patent application are hydrophilic, pressure-sensitive adhesive compositions comprising:

a crosslinked, swellable polymeric matrix formed by a free-radical polymerization of at least one polymerizable monomeric species wherein a majority of the monomeric component is comprised of one or more N-vinyl lactams, and a crosslinker which is a multi-ethylenically unsaturated compound with the ethylenic groups being vinyl, allyl, or methallyl groups bonded to nitrogen or oxygen atoms; and a plasticizer;

wherein the crosslinker and the plasticizer are present in amounts sufficient for the composition to be cohesive, swellable and pressure-sensitive adhesive.

The N-vinyl lactams which comprise a majority of the monomeric portions of the precursor of such an adhesive composition can be selected from the following illustrative group:

N-vinyl-2-pyrrolidone;
5-methyl-N-vinyl-2-pyrrolidone;
5-ethyl-N-vinyl-2-pyrrolidone;
3,3-dimethyl-N-vinyl-2-pyrrolidone;
3-methyl-N-vinyl-2-pyrrolidone;
3-ethyl-N-vinyl-2-pyrrolidone;
4-methyl-N-vinyl-2-pyrrolidone;
4-ethyl-N-vinyl-2-pyrrolidone;
N-vinyl-2-valerolactam;
N-vinyl-2-caprolactam;

and mixtures of any of the foregoing. Preferably, the N-vinyl lactam is N-vinyl-2-pyrrolidone A comonomer such as N,N-dimethylacrylamide can also be used. While other comonomers can be used without adverse results, the majority of the monomer is preferably an N-vinyl lactam.

The crosslinking compounds found to be suitable for preparing such an adhesive composition have vinyl groups, allyl groups, and/or methallyl groups bonded to nitrogen or oxygen atoms Exemplary compounds include divinyl, diallyl or dimethallyl esters (e.g., divinyl succinate, divinyl adipate, divinyl maleate, divinyl oxalate, divinyl malonate, divinyl glutarate, diallyl itaconate, diallyl maleate, diallyl fumarate, diallyl diglycolate, diallyl oxalate, diallyl adipate, diallyl succinate, diallyl azelate, diallyl malonate, diallyl glutarate, dimethallyl maleate, dimethallyl oxalate, dimethallyl malonate, dimethallyl succinate, dimethallyl glutarate, and dimethallyl adipate), divinyl, diallyl or dimethallyl ethers (e.g., diethyleneglycol divinyl ether, butane diol divinyl ether, ethylene glycol divinyl ether, ethylene glycol diallyl ether, diethylene glycol diallyl ether, butane diol diallyl ether, ethylene glycol dimethallyl ether, diethylene glycol dimethallyl ether, and butane diol dimethallyl ether), divinyl, diallyl or dimethallyl amides including bis(N-vinyl lactams), (e.g., 3,3'-ethylidene bis(N-vinyl-2-pyrrolidone)), and divinyl, diallyl or dimethallyl ureas. Presently preferred crosslinking compounds are divinyl adipate, 3,3'-ethylidene bis(N-vinyl-2-pyrrolidone) and diethyleneglycol divinyl ether.

The foregoing electrically-conductive adhesives have been found to be especially useful for incorporations of the ferric/ferrous couple. Table 1 below sets forth the components and amounts used to prepare one preferred embodiment of the interfacing material of the present invention where such an electrically conductive adhesive is involved.

TABLE 1

| Composition | Wt. % Range |
| --- | --- |
| N—vinyl-2-pyrrolidone | 15–60 |
| Potassium Chloride | 0.2–15 |
| Ferrous/Ferric Sulfate [1:1 Molar] | 0.1–10 |
| Water | 10–85 |
| Glycerol | 0–75 |
| Diethyleneglycol divinyl ether (crosslinker) | .1–3 |
| 2-Hydroxy-2-methyl-1-phenyl-1-propanone (photo-initiator) | .1–2 |

Other useful compositions for preparing the interfacing material are electrically-conductive cohesive gels prepared from polymerized acrylic acid (as disclosed in U.S. Pat. No. 4,554,924 to Engel), guar gum (as disclosed in U.S. Pat. No. 4,406,827 to Carim) or polyvinyl alcohol. The preferred components and the preferred ranges of their concentration for use in the present invention are shown below in Tables 2, 3 and 4.

TABLE 2

Polymerized Acrylic Acid Gel

| | Range wt. % lower limit to upper limit |
| --- | --- |
| Water | 10–90 |
| Acrylic Acid | 5–30 |
| Glycerol | 0–80 |
| Ferrous Sulfate | .05–7 |
| Ferric Sulfate | .75–10 |
| Potassium Chloride | 0–10 |
| "Irgacure 651" photo-initiator (Ciba-Geigy) benzildimethylketal | .01–.3 |

TABLE 3

Crosslinked Polyvinyl Alcohol Gel

| | Range wt. % lower limit to upper limit |
| --- | --- |
| PVA (mw. 115000: Aldrich Milwaukee, Wis). | 4–15 |
| Natrosol (250 G.R., Hercules Wilmington, Delaware) | 0–2 |
| Glyoxal (40% aqueous) | 1–15 |
| Glycerol | 0–60 |
| Water | 10–80 |
| Ferrous Sulfate | .1–10 |
| Ferric Sulfate | .1–10 |

TABLE 4

Guar Gum Gel

| | Range wt. % lower limit to upper limit |
| --- | --- |
| Water | 20–90 |
| Guar Gum HP 11 (Celanese Corp., Vernon, Texas) | 1–7 |
| Hydrated potassium tetraborate | .5–5 |
| Propylene Glycol | 0–70 |
| Nitrilotriacetic acid tri-sodium | .5–20 |

TABLE 4-continued

Guar Gum Gel

| | Range wt. % lower limit to upper limit |
|---|---|
| salt (NTANa₃) (Harshaw Chemicals) | |
| Methyl Benzoate | .1–1 |
| Propyl Benzoate | .01–.5 |
| Ferrous Sulfate | .5–10 |
| Ferric Sulfate | .5–10 |
| Potassium hydroxide to adjust pH to a value of from 7.2 to 9 | 7.2–9 |

Alternatives to the pressure-sensitive adhesives and cohesive gels described above are wet gels, i.e., thickened fluids, derived from copolymers of water-soluble monomers and a crosslinking comonomer which are physically sheared in the presence of a liquid to form a thickened fluid. Particularly preferred wet gels are prepared by polymerizing N-vinyl-2-pyrrolidone with a bis(N-vinyl lactam) to form a highly crosslinked copolymer. The copolymer is then subjected to high velocity shear forces, e.g., those provided by a "Waring" blender or the like, in the presence of a liquid such as water, glycerol or a mixture of water and glycerol. An oxidizable and reducible species can then be added to the resulting thickened fluid to produce an interfacing material of this invention.

The third element of this invention is a means for maintaining the interfacing material in contact with the skin. For the bioelectrode to function as intended, the interfacing material should have stable consistent contact with the skin to which the electrode has been applied. Any means which will provide this stable consistent contact are within the contemplation of this invention When the interfacing material is itself a pressure-sensitive adhesive such as that described in Table 1 above, it serves to maintain contact between itself and the skin and no separate means are required. Where the interfacing member is not tacky enough to hold the electrode on the skin, a patch of pressure-sensitive adhesive tape or more complex electrode assemblies known in the bioelectrode art may be used. In particular, a patch of pressure-sensitive tape having an aperture through which a portion of the sensing element may pass will serve as the means for maintaining contact between the interfacing member and skin. Of course, for the assembly to function as a bioelectrode electrical contact must also be maintained between the sensing element member and the interfacing material.

A bioelectrode of the present invention can be constructed by substituting the interfacing material of this invention and, preferably, the sensing element described herein for the interfacing material of any conventional bioelectrode. For example, the cohesive gel interfacing materials of this invention can be used in place of the gel pad of the bioelectrode shown in U.S. Pat. No. 3,805,769 (Sessions), the disclosure of which is incorporated herein by reference. Likewise, the conductive adhesive interfacing materials of this invention can be substituted for the conductive adhesive in the bioelectrode shown in U.S. Pat. No. 4,554,929 (Engel), the disclosure of which is incorporated herein by reference.

The preferred construction is shown in the figures. Bioelectrode 10 in FIG. 1 includes a sensing element shown as an eyelet 20, interfacing material 22 and means 12 for securing the interfacing material to a patient's skin. The sensing element 20 has a base which when assembled contacts the interfacing material along the lower surface of the base. The eyelet also has a post portion integral with the base and suitable for attachment to a conventional snap connection of a lead wire. The means 12 for securing the interfacing material to a patient's skin is shown as a conventional medical tape comprised of backing 14 and pressure-sensitive adhesive 16. The medical tape 12 has a perimeter larger than that of the interfacing material 22 so that an apron of the medical tape surrounds the interfacing material when the electrode is assembled. The medical tape also has an aperture at its center to receive the post of the eyelet.

Figure 2:
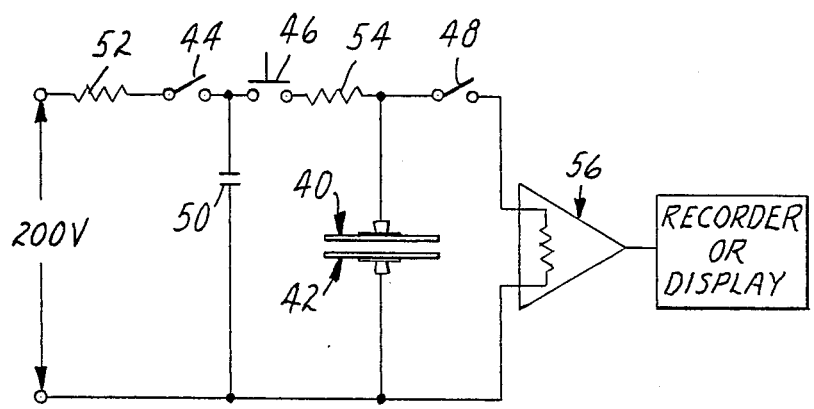
FIG. 2 is a diagram of a circuit for use in an overload recovery test.

As indicated above, the ability of an electrode to recover from a polarizing overload potential can be measured. A standardized test procedure known as the "American National Standard for Pregelled ECG Disposable Electrodes" published by the Association for Advancement of Medical Instrumentation, 1901 North Fort Meyer Drive, Suite 602, Arlington, VA 22209, is suitable. The preferred electrode meets the AAMI Standard, but electrodes that recover to a polarization of 300 millivolts are nonetheless considered within the scope of the invention. To meet the AAMI Standard an electrode must have a Polarization Value at 5 seconds after the 4th pulse in the Polarization Potential Recovery Test of not greater than 100 millivolts. Preferred electrodes also exhibit an offset potential in the DC offset voltage test of not greater than 100 millivolts, and an AC impedance at 10 hertz of not greater than 2,000 ohms. The test methods used to obtain these values are set forth below:

Polarization Potential Recovery Test—This test measures the electrode's ability to permit the ECG trace to return after defibrillation. The circuit for the test is shown in FIG. 2. The test is conducted as follows:

1. The electrodes 40 and 42 are connected gel to gel and connected to the test circuit as described in the AAMI Test Standard, with switch 44 closed and switches 46 and 48 open.
2. At least 10 seconds is allowed for the capacitor to fully charge to 200 V; switch 44 is then opened.
3. The capacitor 50 is discharged through the electrode pair by holding switch 46 closed long enough to discharge the capacitor 50 to less than 2V. This time is no longer than 2 seconds.
4. Switch 48 is closed immediately, and the electrode pair is connected to the offset measurement system (switch 46 open).
5. The electrode offset potential is recorded to the nearest 1 mV, 5 seconds after the closure of switch 48 and every 10 seconds thereafter for the next 30 seconds. The overload and measurement is repeated three times.

The above test sequence (steps 1–5) is repeated for 3 electrode pairs. The polarization potential noted for an electrode of a particular construction is the numerical average of the potentials measured 5 seconds after the fourth pulse for each of the three sample pairs.

In the test circuit (FIG. 2) resistor 52 has a resistance of 10 kilohms, and resistor 54 is a 5 watt, 100 ohm resistor. Compacitor 50 has a capacitance of 10 $\mu$F. All capacitors and resistors are within 90 to 110 percent of the specified values. The offset recorder input amplifier 56 has an input impedance from 0 to 10 Hz of 10 M$\Omega$, ±10 percent, and a bias current of less than 200 nA. The error of the voltage-recording equipment is no greater than ±5 percent of full scale of 100 mV. A 10 mV change is measurable with an error no greater than ±1 mV. For this purpose, the full scale range and resolution of the recording instrument may be adjusted as needed.

The "polarization potential" caused by an overload as here described is also known in the art as the "overpotential" or "stored charge."

DC offset voltage test—The DC offset voltage is measured by connecting two electrodes gel to gel to form a circuit with a DC voltmeter having a minimum input impedance of 10 MΩ and a resolution of 1 mV or better. The measuring instrument applies less than 10 nA of bias current to the electrodes being tested. The measurement is made after a 1 min. stabilization period, but before 1.5 minutes have elapsed.

A pair of electrodes connected gel to gel should, after a 1 minute stabilization period, exhibit an offset voltage no greater than 3 mV and preferably no more than 100 mV.

AC impedance test—The impedance of a pair of electrodes connected gel to gel can be determined by applying a sinusoidal current of known amplitude and observing the amplitude of the resulting potential across the electrodes. The magnitude of the impedance is the ratio of the amplitude of the voltage to the amplitude of the current. An adequate current generator can be assembled utilizing a sinusoidal signal (voltage) generator with a 1-MΩ (or greater) resistor in series with the electrode pair. Preferably the level of the impressed current should not exceed 100 μA peak-to-peak.

The average value of impedance at 10 Hz, determined for at least 12 electrode pairs connected gel to gel, preferably should not exceed 2KΩ. Preferably none of the individual pair impedances should exceed 3KΩ.

EXAMPLES

Interfacing materials

The method of making the Interfacing Material (IM) of each example is shown below. Each interfacing material is identified by a Roman numeral.

Interfacing Material I (IM-I)

A first solution was prepared by adding 0.16 g benzildimethyl ketal ("Irgacure 651", obtained from Ciba-Geigy Company), to 106.4 g of acrylic acid with rapid stirring. To this was added 16 g of a 50% aqueous polyacrylic acid solution ("K739", obtained from B.F. Goodrich Co.) with continued mixing. Separately, glycerol (200 g) was added, with stirring, to deionized water (453.6 g). This solution was added to the acrylic acid solution and shaken on a reciprocating laboratory shaker (Eberbach, Ann Arbor, Michigan) for several hours, using an air-tight glass vessel, wrapped with aluminum foil to minimize exposure to ambient U.V. light. After the shaking was completed, the resulting solution was poured into a glass tray, and was illuminated for about 2.5 minutes by the light from six 15 watt U.V. lamps ("Blacklight" tubes FIST8-BL, General Electric) at a distance of about 7 cm under a nitrogen atmosphere. The resulting solution was called Stock Solution 1.

Ferric EDTA (ferric EDTA, monosodium salt, Alfa Inorganics, Danvers, Mass.) (10.95 g) was added to warm deionized water (97 g) and stirred until dissolved. Separately, ferrous gluconate (21.95 g) (Alfa Inorganics, Danvers, Mass ) was added to deionized water (49.05 g); and to this was added glycerol (15 g). The mixture was warmed and stirred to dissolve the gluconate. Another separate solution was prepared by adding ferric sulfate (hydrated) (19.26 g) to glycerol (40.74 g) and deionized water (15 g) The mixture was warmed and stirred until the ferric sulfate was dissolved.

In a "Waring Blendor", to a sample of Stock Solution 1 (40 g) was added glycerol (10 g), ferric EDTA solution (11.5 g) and ferrous gluconate solution (9 g) at low to medium speed, with continued mixing, to this mixture the solution of ferric sulfate (2 g) was added slowly. A well crosslinked gel was obtained. (It is noteworthy that crosslinkers other than ferric sulfate may also be used.)

To one-half the weight of the gel obtained above was added with mixing in the blender an ascorbic acid solution (0.1 g ascorbic acid in 1 g water) (Ascorbic Acid, MCB, Norwood, Ohio). The pH of the above resulting gel was adjusted to 4.5 with a 20% solution of NaOH. A crosslinked gel was obtained, which was put between two sheets of silicone treated release paper and the whole was sealed in a moisture-impermeable plastic bag (aluminized polyethylene) between metal plates to flatten it into a sheet of gel a few millimeters thick. Pieces of Volara ®polyethylene foam (obtained from Voltek, Inc., Lawrence, Mass ) were cut in the shape of electrode backings and were then coated on one side with a standard medical grade acrylic acid/isooctyl acrylate pressure-sensitive adhesive. Eyelets, namely, #304 stainless steel eyelets (TRW Co., Waterbury, CT) were inserted in the foam shapes to serve as the sensing elements.

The gel of Example 10 was prepared by similar methods but had the composition below:

| | wt. % |
|---|---|
| Water | 60.00 |
| Acrylic Acid | 7.97 |
| Glycerol | 30.00 |
| Ferrous Sulfate | .50 |
| Ferric Sulfate | .75 |
| Potassium Chloride | .75 |
| "Irgacure 651" photo-initiator (Ciba-Geigy benzildimethylketal) | .03 |

Interfacing Material II (IM-II)

One way of utilizing this invention is to have the oxidizable and reducible species in an aqueous solution absorbed in a sponge in contact with a stainless steel sensing element. The above scheme is exemplified as follows. To a 358.3 g sample of deionized water, was added 22.108 g of $FeSO_4 7H_2O$ and 19.6 g of $Fe_2(SO_4)_3 5H_2O$ and stirred to dissolve. The composition, therefore, was as shown below.

| | % Wt. | Molar |
|---|---|---|
| Water | 89.6 | — |
| $FeSO_4 \cdot 7H_2O$ | 5.5 | .36 |
| $Fe_2(SO_4)_3 \cdot 5H_2O$ | 4.9 | .12 |

Electrode backings made from Volara ® polyethylene foam (Voltek, Inc., Lawrence, Mass.) and coated on one side with a medical grade adhesive were fitted with stainless steel eyelets, and a polyurethane sponge soaked with the solution above was placed between a pair of such electrodes. The spacing between eyelets (electrodes) was approximately 0.5 cm.

Interfacing Material III (IM-III)

Interfacing Material II was repeated with the exception that the ferric and ferrous sulfates were replaced by sufficient sulfuric acid to obtain the same pH (1.64).

Interfacing Material IV (IM-IV)

To 40 g of deionized water was added 23 g of glycerol with mixing in a 'Waring' blender. To this was added 7 g of polyvinyl alcohol (MW-115000; [Aldrich, Milwaukee, Wis.]) and 2.16 g of 'Natrosol'—hydroxyethyl cellulose thickener—(#250 G. R. Hercules, Wilmington, Del.) This was mixture A. Separately in a beaker containing 20 g deionized water, 1.33 g of $FeSO_4$ (unhydrated) and 1.83 g of $Fe_2(SO_4)_3$ (unhydrated) were dissolved. This solution was then mixed with mixture A. Subsequently, with vigorous blending, 4.66 g of ethanedial 40% solution (glyoxal) was added slowly. A good gel was obtained, greasy to touch. After 3 weeks of aging at room conditions and 10 days at 120° F. in a convection oven (Blue-M Co.), the gel had a pH of about 2.2 and was tested in electrodes with stainless steel sensing elements as described in Example 1.

Interfacing Material V (IM-V)

The procedures used to prepare Interfacing Material IV were repeated with the following amounts:

|  | wt. % |
|---|---|
| PVA (mw. 115000: Aldrich Milwaukee, Wis.) | 7.00 |
| Natrosol (250 G.R., Hercules Wilmington, DE) | .75 |
| Glyoxal (40% aqueous) Fisher Scientific, Fairlawn, NJ | 6.00 |
| Glycerol | 15.00 |
| Water | 64.25 |
| Ferrous Sulfate | 3.00 |
| Ferric Sulfate | 4.00 |

Interfacing Material VI (IM-VI)

To an amber colored glass bottle, were added NVP (N-vinyl-2-pyrrolidone 98%, Aldrich Chemical Co., Milwaukee, Wisconsin), glycerol, and water as shown in Table 5. When potassium chloride was added, it was pre-dissolved in the water. These were mixed well by shaking. This was called Mixture A. To mixture A was added diethyleneglycol divinyl ether (0.8 g, GAF) and 2-hydroxy-2-methyl-1 -phenyl-1-propanone (0.4 g, E.M. Scientific, Gibbstown, NJ) and the mixture was shaken well for 5 minutes. This was called Mixture B. The following Table 5 shows the particular amounts of each component for each of Examples 5–9.

TABLE 5

| | Conductive Adhesive Composition | | | | |
|---|---|---|---|---|---|
| Example No. | 5 | 6 | 7 | 8 | 9 |
| NVP | 32.00 | 32.00 | 32.00 | 32.20 | 33.00 |
| Potassium Chloride | .50 | .50 | 00.00 | 00.00 | 00.00 |
| Ferrous/Ferric Sulfate [1:1 Molar] | .50 | 1.00 | .50 | 1.00 | 2.00 |
| Water | 13.18 | 12.68 | 13.68 | 13.18 | 41.00 |
| Glycerol | 53.00 | 53.00 | 53.00 | 53.00 | 24.80 |
| Diethyleneglycol divinyl ether [cross linker] | .50 | .50 | .50 | .50 | 0.80 |
| 2-hydroxy-2-methyl-1-phenyl-1-propanone [photo-initiator] | .32 | .32 | .32 | .32 | 0.40 |

A mold was prepared from silicone-treated polyester sheeting (0.05 mm thick) and a Teflon spacer. The spacer had an inside rectangular window of about 7.5 ×12.5 cm and was 1 mm thick. It was placed upon a sheet of the silicone-treated polyester sheet, with a little silicone grease to ensure a good seal. Mixture B was poured into and filled the cavity formed by the Teflon spacer, and a second silicone-treated polyester sheet was placed over it in contact with its surface.

The whole mixture was illuminated for about 10 minutes by a sunlamp (Sylvania, 275 watts) placed about 15 cm above it. This caused the mixture to polymerize to a crosslinked pressure sensitive adhesive, which was obtained as a thin (1 mm) layer on the polyester sheeting or liner. A sample of this adhesive, weighing about 10 g, was cut from the bulk and ferrous and ferric sulfate hydrates (Fluka AG, Switzerland) were separately added to the surface as finely-divided powders in the amounts shown in Table 5. These salts were allowed to diffuse into the adhesive over 4 days, in a sealed plastic bag. A yellowish conductive adhesive wa obtained.

This adhesive was tested by making electrodes, using carbon-resin eyelets (Fiberite Corp. FM 32785) as the sensing element, as described in the previous examples.

Interfacing Material VII (IM-VII)

The following materials were mixed together in a blender ("Waring Blendor") operating at medium speed. They were added in the following order:

1. Propylene glycol (30 g), methyl benzoate (0.2 g), and propyl benzoate (0.04 g). These were mixed until the benzoates were both dissolved.
2. Guar gum (7.5 g), HP11, Celanese Co., powder, was added to the solution.

In a separate vessel, anhydrous ferrous sulfate (3.5 g), anhydrous ferric sulfate (6.0 g) and the monosodium salt of nitrilotriacetic acid (9.5 g) were dissolved in water (120 ml). This solution was added to the mixture already prepared in the blender. Mixing at medium/high speed was continued until a smooth paste was formed. This took about 10 minutes.

A solution was prepared by mixing hydrated potassium tetraborate (3.5 g) in about 20 ml deionized water, which was added to the mixture in the blender, while continuing to stir at medium/high speed. The viscosity of the mixture increased visibly, and a gel was quickly obtained. Blending was continued for 3-4 minutes. At this time blending was stopped and a sample of the gel was removed and its pH measured with a pH meter to the nearest 0.1 pH unit. A few drops of 20% sodium hydroxide solution were added to the whole to bring its pH to 7.5-8.0.

The gel was stored in a sealed glass jar at ambient temperature for about 10 days, and was then made into electrodes in the following manner.

Electrode backings made from Volara ® polyethylene foam (Voltek, Inc., Lawrence, Mass.) and coated on one side with a medical grade adhesive were fitted with graphite/resin eyelets (Cat. No. FM 49609, Fiberite Corp., Winona, Minnesota), and then filled with the gel made above (2–3 g). They were made in pairs and assembled together gel to gel, and stored in room conditions in a sealed plastic bag for seven days. Electrical property tests were then made. (See Example 12, Table 7).

Interfacing Material VIII (IM-VIII)

Glycerol (60 g) was poured into a 'Waring' blender and 0.2g of methyl p-hydroxy-benzoate (Matheson Coleman Bell, Norwood, Ohio) with 0.04 g of propyl p-hydroxy-benzoate (Eastman Kodak & Co., Rochester, N.Y.) were added and mixed well. To this mixture 4 g of guar gum No. C13 (Celanese Corp., Vernon, Texas) was added and blended. This was mixture A. Separately, in a beaker, 10 g of potassium chloride was dissolved in 90 g of deionized water. This was solution B. In another beaker containing 35 g deionized water, 0.8 g of ethylenediaminetetraacetic acid iron (III) monosodium salt and 0.8 g of iron (II) ethylenediamine ammonium sulfate (Alfa Products, Danvers, MA) were dissolved. This was solution C.

With blending, the solution B was added to mixture A for 5 to 10 minutes, allowing the resultant mixture D to heat to approximately 50° ±5° C. Subsequently, solution C was added to mixture D and blended for 2–4 minutes, then poured into a glass jar and sealed. The pH of this final viscous gel sample at room temperature was pH=4.

The jar of gel was aged in a heated oven at 77° C. for 2 days and at room conditions for 18 days before testing in electrodes.

Interfacing Material IX (IM-IX)

To a 30 g sample of glycerol in a 'Waring' blender was added 2.5 g of hydroxyethyl cellulose QP 300 (Union Carbide) and 1.5 g of 'Carbopol'934 (B.F. Goodrich). This was mixture A. Separately, in a beaker containing approximately 35 g deionized water, 1 g of sodium sulfate decahydrate (Fisher Scientific) was dissolved, and this solution was added with blending to mixture A to give mixture B. Separately, in another beaker containing 17 g of deionized water, 2.5 g of ethylenediaminetetraacetic acid (Iron II) monosodium salt (Alfa Products, Danvers, MA) was dissolved and subsequently 1.1 g of ascorbic acid powder was dissolved. This mixture was then added to mixture B and a slightly viscous liquid was obtained. A total of 18 cc of a 10% NaOH solution was added with blending and the pH raised from 3.3 to 6.3. A gray-green very viscous gel was obtained.

Interfacing Material X (IM-X)

A first solution was prepared by adding benzildimethylketal ("Irgacure 651", obtained from Ciba Geigy), 0.28 g to acrylic acid, 100 g, with rapid stirring. To this was added a 50% aqueous polyacrylic acid solution, 8 g, ("K739", obtained from B.F. Goodrich Co.), with continued mixing. Separately, glycerol (250 g) and sodium sulfate (4 g) were added, with stirring, to deionized water (500 g). This solution was added to the acrylic acid solution and shaken on a reciprocating laboratory shaker (Eberbach, Ann Arbor, Michigan) for several hours, using an air-tight glass vessel, wrapped with aluminum foil to minimize exposure to ambient U.V light. After the shaking was completed, the resulting solution was poured into a glass tray, and was illuminated for about 2.5 minutes by the light from six 15 watt U.V. lamps. ("Blacklight" tubes F1ST8-BL, General Electric) at a distance of about 7 cm, under a nitrogen atmosphere. The resulting solution was called Stock Solution 1.

Ferrous sulfate, $FeSO_4.7H_2O$, (10.95 g) and ferric sulfate, $Fe_2(SO_4)_3.5H_2O$, (19.26 g) were each separately dissolved in aqueous glycerol (glycerol 49.05 g/water 15 g and 40.74 g/water 15 g respectively), using vigorous stirring and gentle warming. The two resulting solutions were then combined and called Stock Solution 2.

Finally, in a blender ("Waring Blendor"), Stock Solution 1 (200 g) was added to a solution of Stock Solution 2 (50 g), which had been diluted with an additional amount (50 g) of glycerol, with vigorous stirring, using the blender at high speed for several seconds.

Interfacing Material XI (IM-XI)

To a sample of N-vinyl-2-pyrrolidone (NVP) weighing 200 g was added 1.35 g of 3,3'-ethylidene- bis(N-vinyl-2-pyrrolidone) (EBVP) as a crosslinker, and 0.95 g of a photoinitiator available from Ciba-Geigy as Duracure ™ DC1173. This mixture was stirred to dissolve the components. This was solution A. Water (deionized) weighing 698.9 g was added to solution A and stirred to form a homogeneous solution. This was solution B. A sample of the solution B weighing about 300 g was poured into an aluminum foil tray of dimensions 19 cm ×29 cm, in a box continuously purged with nitrogen gas and covered with a quartz plate. The sample was exposed to ultraviolet light (UV) from two Sylvania RSM "sunlamps" through the quartz plate. The tray was removed after several minutes of UV exposure and a clear, crumbly, approximately 0.6 cm thick sheet was obtained. The composition of this precursor C was as follows.

| Ingredient | Wt. % |
|---|---|
| N—vinyl-2-pyrrolidone (NVP) | 22.2 |
| Water (deionized) | 77.5 |
| 3,3'-Ethylidene-bis(N—vinyl-2-pyrrolidone) (EBVP) | 0.15 |
| Photoinitiator* | .105 |
| Total approx. | 100 |

*Duracure ™ (DC1173) available from Ciba-Geigy

The ratio of NVP to water was 1:3.5 with a 0.15% level of the crosslinker EBVP. Too high a crosslinker level will give a precursor that will not swell to form a wet gel; too little will give a stringy, sticky gel.

The cured precursor "C" was used as follows. A sample of "C" weighing 112.5 g was put in a "Waring" blender and 80 g of glycerol was added to it. Separately, to 20 g of glycerol was added 1.11 g of methyl p-hydroxybenzoate and 0.11 g of propyl p-hydroxybenzoate and the mixture was heated to dissolve the benzoates and subsequently added to the precursor-glycerol in the blender; this was called mixture "D". Separately, in 200 g of water, ferric ammonium citrate weighing 15 g and 15 g of ferrous sulfate (hydrated) were dissolved and the solution added to mixture D above in the blender and mixed well at high speed. This was called gel "E". To 94.5 g of gel E was added 8.5 g of water to give a final gel composition as shown below having a pH of about 3.

| Ingredient | approx. Wt. % |
|---|---|
| NVP | 05.200 |
| EBVP | 00.035 |
| Photoinitiator | 00.024 |
| Glycerol | 20.700 |
| Ferric Ammonium Citrate | 03.100 |
| Hydrated Ferrous Sulfate (7 $H_2O$) | 03.100 |
| Water | 67.700 |

| Ingredient | approx. Wt. % |
|---|---|
| Total | approx. 100% |

The final wet gel is a smooth paste, much like mayonnaise or tooth paste gel.

EXAMPLES 1-4

The Interfacing Materials IM-I, IM-II, IM-III and IM-IV were used to prepare bioelectrodes with stainless steel sensing elements. These bioelectrodes were tested as described above to yield the results shown in Table 6.

TABLE 6

Stainless Steel Sensing Elements With Redox Couple

| Ex. No. | IM | pH | Half Cell Potential With Ref. to AgCl (mV) | DC Offset Voltage (mV) | AC Impedance ($\Omega$ @ 10 Hz) | Polarization Value (mV at 5 sec/ 35 sec after 4th pulse) |
|---|---|---|---|---|---|---|
| 1 | I | 4.5 | 42 | 1.4 | 940 | 799/432 |
| 2 | II | 1.64 | −458 | 0.6 | 940 | 5.3/0.7 |
| 3 | III | 1.64 | −492 | 8.5 | 1260 | 1022/837 |
| 4 | IV | 2 | −431 | .2 | 1300 | 57/3 |

In Table 6, note that the higher pH gel of Example 1 may have reduced the concentration of free ferric and ferrous ions in solution such that the electrode exhibits an undesirably high polarization value of 799 mV compared to Example 4 where the value is 57 mV, which gel had a pH of about 2. A comparison of Examples 2 and 3 shows the utility of a redox couple to reduce the polarizability of the electrode.

EXAMPLES 5-12

Interfacing Material IM-I, IM-V, IM-VI and IM-VII were tested as described above in bioelectrodes as described below.

Eyelets of 25% resin material available from Fiberite Corp., Winona, MN. Material #FM496090, were assembled with Volara® polyethylene foam backing (Voltek Inc.m Lawrence, Mass.) coated on one side with a medical grade adhesive, and discs of the above adhesives (about 3 mm. thick × 15 mm dia.) were placed between the eyelets of pairs of electrodes. Electrodes were stored 2-5 days in a sealed glass jar which also contained a few cc. of water in an open bottle. This procedure added a maximum of 10% water to the samples of Examples 5-8 and 2% to the sample of Example 9 (Table 7) respectively.

TABLE 7

| Ex. No. | IM | DC Offset Voltage (mV) | AC Impedance (@ 10 HZ OHMS) | AC Impedance (@ 100 KHZ OHMS) | Polarization (mV @ 5 sec. after 4th pulse/ mV @ 35 sec. after 4th pulse) |
|---|---|---|---|---|---|
| 5 | VI | 9.9 | 1700 | 1300 | 70/30 |
| 6 | VI | 12.3 | 2100 | 1600 | 76/30 |
| 7 | VI | 0 | 1100 | 810 | 67/32 |
| 8 | VI | 3 | 790 | 520 | 44/22 |
| 9* | VI | 2.5 | 1400 | 900 | 49/21 |
| 10 | I | .5 | 190 | 13 | 58/20 |
| 11 | V | .1 | 42 | 9.2 | 14/7.7 |
| 12 | VII | 1.5 | 230 | 5 | 40/13 |

*eyelet was 30% resin

EXAMPLES 13-16

Samples of IM-VIII were tested with various sensing elements as described below. Polyethylene foam (Volara®, Voltek Inc., Lawrence, Mass.) coated on one side with a medical grade adhesive was fitted with the following carbon-graphite containing eyelets (sensing elements) of approximately equal geometric surface area and filled with the IM-VIII. Two pairs each were tested in accordance with tests described above. The following sensing elements were used.

Sensing elements

S & E - Schunk and Ebe, W. Germany Cat. No. 30-120-1-32625/2 Grade HG31
RTP-F - RTP Corporation, Winona, MN
RTP-H - RTP Corporation, Winona, MN
RTP-84056 - RTP Corporation, Winona, MN The resistance of the sensing elements was measured as the average value of a number of them using a Fluke model 8520A digital D.C. multimeter with 'pencil point' probes placed firmly on the circular perimeter of the conductor, across a diameter.

Except for the S & E, all other sensing elements were abraded by hand with a 3M brand 240 grit silicon carbide sandpaper (3M, St. Paul, MN)

Electrical test results are shown in Table 8.

TABLE 8

Electrode Performance Data

| Ex. No. | Conductor | Resistance (Ohms) | DC Offset Voltage (mV) | AC Impedance (@ 10 HZ in Ohms/per Pair) |
|---|---|---|---|---|
| 13 | S & E | <1 | 1 | 195 |
| 14 | RTP-F | 7 | 2 | 1250 |
| 15 | RTP-H | 90 | 9 | 450 |
| 16 | RTP-84056 | 300 | 35 | 35000 |

The data above show that for this composition there is no strict correlation between resistance and impedance although there is a general trend that lower resistance sensing elements show lower impedance. The offset potential, however, shows higher values and more instability as the resistance of the sensing element increases.

The impedance values may be lowered by either using a sensing element with a larger surface area or a gel composition with a higher concentration of iron salts.

The sensing element resistance should preferably be as small as possible to flow a low resistance contact with the connection to the biopotential monitoring equipment, to reduce the magnitude of environmental electromagnetic field induced artifacts, and to form a more nonpolarizable interface with the interfacing material.

The gel composition used above contains the iron salts which provide the non-polarizability aspect of the electrode's performance and the potassium chloride salt functions primarily to lower the gel skin impedance. It has been found that as the concentration of the chloride salt is increased, e.g., from 0.1% by weight to 10%, the impedance of the gel is significantly reduced.

This invention, therefore, allows independent control of the polarizability of the electrode and its ability to lower skin impedance. In prior art electrodes, an increase in the salt (KCl) concentration causes an increase in the probability of corrosion of the snap and deterioration of the silver-silver chloride plating of the sensing element.

EXAMPLE 17

A sample of IM-IX was put in a glass jar, sealed, and then stored at room conditions. Three years and eight months later, a portion of this gel was removed and assembled into electrodes having polyethylene foam (Volara®, Voltek, Inc. Lawrence, Mass.) electrode blanks coated on one side with a medical grade adhesive and fitted with RTP-G (RTP Corp, Winona, MN) abraded carbon-graphite conductors; electrode pairs were tested in accordance with the above tests, and the resultant data is shown below.

DC Offset voltage = 10 mV
AC Impedance @10Hz = 76 ohms
Polarization value @5 sec. after 4th pulse = 27 mV The above example illustrates the very long shelf-life of a representative interfacing material useful in this invention.

EXAMPLE 18

The following shows the effect of aging on a polyacrylic acid gel.

IM-X, a gel, was placed between two sheets of silicone-treated release paper and the whole was sealed in a moisture-impervious plastic bag (aluminized polyethylene). The product was stored in an oven at 50° C. between metal plates to flatten the gel to a thickness of approximately 3 mm. This gel was used in making test electrodes, using polyethylene foam (Volara®, Voltek, Inc., Lawrence, Mass.) coated on one side with a medical grade adhesive and using SE (Schunk and Ebe - West Germany) graphite eyelets as the sensing elements. The electrodes were tested as described above with results as follows in Table 9:

TABLE 9

| Days Aged at 50° C. | DC Offset Voltage (mV) | AC Impedance Ω @ 10 Hz | Polarization Value (mV @ 5 Sec. after 4th Pulse) |
|---|---|---|---|
| 7  | 1.8 | 287 | 75 |
| 14 | 1.6 | 161 | 88 |
| 21 | 0   | 159 | 53 |
| 28 | .2  | 167 | 60 |
| 35 | 0   | 160 | 59 |
| 42 | .1  | 178 | 70 |
| 60 | .3  | 208 | 67 |
| 84 | .1  | 218 | 80 |

EXAMPLES 19–21

Wet Gels

In each of Examples 19–2an electrode was made with IM-XI, polyethylene foam (Volara®, Voltek, Inc., Lawrence, Mass.) coated on one side with a medical grade adhesive, and RTP-G carbon eyelets (RTP Corp. Winona, MN) The electrodes of Example 19 were stored in sealed bags for two weeks at about 50° C. The electrodes of Example 20 were stored at room temperature (about 22° C.) for two weeks, and those of Example 21 were stored at about 50° C. for eight weeks. The data is shown below.

| Example | pH | Offset (mV) | Impedance (@ 10 Hz) | Polarization (mV @ 5 sec. after 4th pulse) |
|---|---|---|---|---|
| 19 | 2.2 | 3 | 138 | 65 |
| 20 | 2.3 | 1 | 155 | 102 |
| 21 | 2.5 | 1 | 160 | 62 |

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A bioelectrode comprising:
   (a) an electrically-conductive, sensing element;
   (b) a dermatologically compatible, electrically-conductive interfacing material in electrical contact with the sensing element, the interfacing material containing an oxidizable species and a reducible species; and
   (c) means for maintaining the interfacing material in contact with skin;
   wherein the sensing element is electrochemically inert in the presence of the interfacing material and wherein the oxidizable and reducible species are galvanically active and are present in amounts sufficient for the bioelectrode to recover from overload potentials 2. A bioelectrode in accordance with claim 1, wherein the oxidizable and reducible species are comprised of a ferrous/ferric redox couple.

3. A bioelectrode in accordance with claim 2, wherein the interfacing material is further comprised of a biologically acceptable complexing agent.

4. A bioelectrode in accordance with claim 3, wherein the complexing agent is ethylenediaminetetraacetic acid.

5. A bioelectrode in accordance with claim 3 wherein the complexing agent is nitrilotriacetic acid.

6. A bioelectrode in accordance with claim 1, wherein the sensing element is comprised of a conductive form of carbon, a noble metal or stainless steel.

7. A bioelectrode in accordance with claim 6, wherein the sensing element is comprised of graphite.

8. A bioelectrode in accordance with claim 7 wherein the graphite is dispersed in a polymeric binder.

9. A bioelectrode in accordance with claim 1, wherein the means for maintaining the interfacing material in contact with the skin comprises a medical tape comprised of a backing and a pressure sensitive adhesive coating on one surface of said backing, the tape having an aperture which receives the sensing element and the pressure sensitive adhesive serving to attach the backing to the interfacing material.

10. A bioelectrode in accordance with claim 1, wherein said interfacing material comprises an electrically-conductive adhesive, the adhesive nature of said electrically-conductive adhesive serving as said means for maintaining the interfacing material in contact with the skin.

11. A bioelectrode in accordance with claim 10, wherein the electrically-conductive adhesive is a hydrophilic, pressure-sensitive adhesive composition comprising:

a crosslinked, swellable polymeric matrix formed by a free-radical polymerization of at least one polymerizable monomeric species wherein a majority of the monomeric component is comprised of one or more N-vinyl lactams, and a crosslinker which is a multi-ethylenically unsaturated compound with the ethylenic groups being vinyl, allyl, or methallyl groups bonded to nitrogen or oxygen atoms; and a plasticizer;

wherein the crosslinker and the plasticizer are present in amounts sufficient for the composition to be cohesive, swellable and pressure-sensitive adhesive.

12. A bioelectrode in accordance with claim 11, wherein said N-vinyl lactams comprise N-vinyl-2-pyrrolidone.

13. A bioelectrode in accordance with claim 12, wherein said plasticizer comprises glycerol.

14. A bioelectrode in accordance with claim 13, wherein said crosslinker comprises diethyleneglycol divinyl ether.

15. A bioelectrode in accordance with claim 1, wherein said interfacing material comprises an electrically-conductive gel comprising:

fragments of a crosslinked, swellable polymeric matrix formed by a free-radical polymerization of at least one polymerizable monomeric species wherein a majority of the monomeric component is comprised of one or more N-vinyl lactams, and a crosslinker which is a multi-ethylenically unsaturated compound with the ethylenic groups being vinyl, allyl, or methallyl groups bonded to nitrogen or oxygen atoms, said fragments being formed by subjecting said crosslinked polymeric matrix, once formed, to shear forces sufficient to cause fragmentation of the polymeric matrix; and a plasticizer.

16. A bioelectrode in accordance with claim 15, wherein said N-vinyl lactams comprise N-vinyl-2-pyrrolidone.

17. A bioelectrode in accordance with claim 16, wherein said plasticizer comprises glycerol.

18. A bioelectrode in accordance with claim 17, wherein said crosslinker comprises 3,3'-ethylidene-bis(N-vinyl-2-pyrrolidone).

* * * * *

UNITED STATES PATENT AND TRADEMARK OFFICE
CERTIFICATE OF CORRECTION

PATENT NO. : 4,846,185

DATED : July 11, 1989

INVENTOR(S) : Hatim M. Carim

It is certified that error appears in the above-identified patent and that said Letters Patent is hereby corrected as shown below:

Col. 1, Line 49, after "instruments" insert a period.

Col. 2, Line 20, after "element" insert a period.

Col. 2, Line 39, "}" should be --)--.

Col. 3, Line 42, insert a period after "etc".

Col. 4, Line 11, insert a period after "preferred".

Col. 5, Line 43, insert a period after "N-vinyl-2-pyrrolidone".

Col. 5, Line 51, insert a period after "atoms".

Col. 10, Line 2, insert a period after "(15g)".

Col. 10, Line 52, "$FeSO_4 7H_2O$" should be --$FeSO_4 \cdot 7H_2O$--.

Col. 10, Line 53 "$(SO_4)_3 5H_2O$" should be --$(SO_4)_3 \cdot 5H_2O$--.

Col. 11, Line 30, insert a comma after "Aldrich".

Col. 11, Line 31, insert a comma after "Hercules".

Col. 12, Line 68, insert a space after "Waring".

Col. 13, Line 25, insert a space after "Waring".

Col. 13, Line 27, insert a space after "'Carbopol'".

Col. 13, Line 35, "II" should be --III--.

UNITED STATES PATENT AND TRADEMARK OFFICE
CERTIFICATE OF CORRECTION

PATENT NO. : 4,846,185

DATED : July 11, 1989

INVENTOR(S) : Hatim M. Carim

It is certified that error appears in the above-identified patent and that said Letters Patent is hereby corrected as shown below:

Col. 15, Line 41, after "Inc." delete "m" and insert therefor --,--.

Col. 17, Line 61, delete "2" and insert therefor --21,-- with a space thereafter.

Col. 17, Line 65, insert a period after --)--.

Signed and Sealed this

Twenty-second Day of May, 1990

Attest:

HARRY F. MANBECK, JR.

*Attesting Officer*       *Commissioner of Patents and Trademarks*